United States Patent [19]

Takatsuki et al.

[11] Patent Number: 5,098,927
[45] Date of Patent: Mar. 24, 1992

[54] ANTIRETROVIRAL AGENT, METHOD OF USE THEREAS, AND METHOD OF PREPARATION

[75] Inventors: Kiyoshi Takatsuki; Yohsuke Maeda; Toshio Hattori, all of Kumamoto; Tsutomu Kaizu; Masanori Okamoto, both of Tsukuba; Yoshiko Yokota, Ibaraki; Katsuya Nakamura, Kobe; Hiroshi Kayakiri, Tsukuba, all of Japan

[73] Assignee: Fujisawa Pharmaceutical Co., Ltd., Osaka, Japan

[21] Appl. No.: 638,159

[22] Filed: Jan. 10, 1991

Related U.S. Application Data

[63] Continuation of Ser. No. 520,060, May 3, 1990, abandoned.

[30] Foreign Application Priority Data

May 15, 1989 [JP] Japan .................................. 1-22291

[51] Int. Cl.[5] .................... C07D 207/12; A61K 31/40
[52] U.S. Cl. .................................... 514/425; 548/541; 548/544
[58] Field of Search ................. 548/541, 544; 514/425

[56] References Cited

U.S. PATENT DOCUMENTS 2,810,726 10/1957 Howard ............................... 548/541

FOREIGN PATENT DOCUMENTS 62-36355  2/1987  Japan .
1114676   9/1984  U.S.S.R. .............................. 548/544
2040933   9/1980  United Kingdom .................. 548/541

OTHER PUBLICATIONS

H. Paulsen et al.; Chem. Ber. 102, 469–487 (1969).
S. Inouye et al.; Tetrahedron 23, 2125–2144 Programun Press (1968).
R. A. Gruters et al.; Nature, 330, 5. Nov. (1987), 74–77.
P. S. Sunkara et al.; Biochemical and Biophysical Research Communications, 148, 1, 206–210 (1987).

*Primary Examiner*—David B. Springer
*Attorney, Agent, or Firm*—Oblon, Spivak, McClelland, Maier & Neustadt

[57] ABSTRACT

Pyrroline compounds of the formulae (I) and (II) are effective in the treatment of retroviral infection and lymphadenopathy.

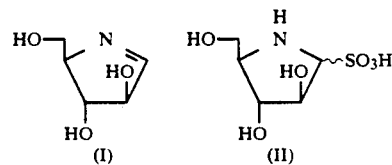

12 Claims. No Drawings

ANTIRETROVIRAL AGENT, METHOD OF USE THEREAS, AND METHOD OF PREPARATION

This application is a continuation of application Ser. No. 07/520,060, filed on May 3, 1990, now abandoned.

This invention relates to a method for treating infectious diseases caused by retrovirus which comprises administering a specific pyrroline compound or its sulfurous acid adduct, or a pharmaceutically acceptable salt thereof to human or animals. The compound used in the present invention produces, inter alia, excellent prophylactic and/or therapeutic effects on human immunodeficiency virus infection. The compound is, thus, useful in the field of medicine.

Retroviruses, whose genome is ribonucleic acid (RNA) are known as viruses causing leukemia, infectious anemia, neoplastic diseases, and the like, in fowls, mammals and various other animals.

In recent years, the occurrence of human retroviruses has been suggested and such human retroviruses as HTLV-I, HTLV-II and human immunodeficiency virus (HIV), which are pathogens causing certain types of leukemia or acquired immunodeficiency syndrome (AIDS), have been discovered. In particular, it is known that HIV infects T-lymphocyte and causes cell death by its cytopathic effect. HIV has been identified as a virus causative of AIDS and AIDS-related complex (ARC). AIDS and ARC are highly lethal, causing high proportions of deaths among patients with AIDS or ARC. Therefore, the advent of a prophylactic and/or therapeutic agent therefor has been earnestly waited for.

As a result of intensive investigations, the inventors of this invention found that a pyrroline compound (I) having the formula given below, which has activity against immunosuppressive factors and α-glucosidase inhibiting activity, or the sulfurous acid adduct (II) derived therefrom, which is a novel compound, or a pharmaceutically acceptable salt thereof can produce excellent prophylactic and therapeutic effects on infectious diseases caused by retrovirus, in particular infectious diseases caused by human immunodeficiency virus. The present invention has been completed based on this novel finding.

It was also found that said novel sulfurous acid adduct (II) derived from the pyrroline compound (I) or a pharmaceutically acceptable salt thereof has anti-inflammatory activity as well.

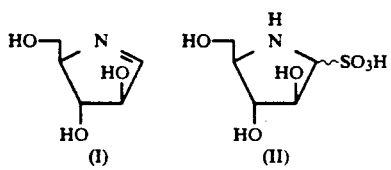

Accordingly, the invention provides a method for treating infectious diseases caused by retrovirus which comprises administering the pyrroline compound (I) or the sulfurous acid adduct (II) derived therefrom, or a pharmaceutically acceptable salt thereof to human or animals.

The invention further provides the novel sulfurous acid-pyrroline adduct (II) and a pharmaceutically acceptable salt thereof, a process of preparing the same, a pharmaceutical composition comprising the same as an active ingredient, and its use.

Preferred examples of the pharmaceutically acceptable salt of the pyrroline compound (I) or its sulfurous acid adduct (II) are conventional nontoxic salts, for example, inorganic salts such as alkali metal salts (e.g. sodium salt, potassium salt), alkaline earth metal salts (e.g. calcium salt, magnesium salt), other metal salts and ammonium salt; organic salts, such as organic amine salts (e.g. trimethylamine salt, triethylamine salt, pyridine salt, procaine salt, picoline salt, dicyclohexylamine salt, N,N-dibenzylethylenediamine salt, N-methylglucamine salt, diethanolamine salt, triethanolamine salt, tris(hydroxymethyl)aminomethane salt, phenylethylbenzylamine salt, dibenzylethylenediamine salt); organic carboxylic or sulfonic acid salts (e.g. formate, acetate, trifluoroacetate, maleate, tartarate, methanesulfonate, benzenesulfonate, toluenesulfonate); inorganic acid salts (e.g. hydrochloride, hydrobromide, sulfate, phosphate); salts with basic or acidic amino acids (e.g. arginine, aspartic acid, glutamic acid, lysine); and salts with zwitter-ions (e.g. betaine).

Under certain conditions, the pyrroline compound (I) may occur in the following equilibrium state in aqueous solution:

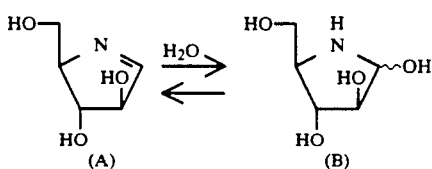

Both of these forms can be used in the practice of the invention and it is to be noted that, in this specification, the form represented by the structural formula (B) should be included in the scope of the pyrroline compound defined by the structural formula (A).

Since a pyrrolidine has an asymmetric carbon atom at position 2 in its cyclic ring, the pyrroline-sulfurous acid adduct (II) includes α isomer, β isomer and a mixture of these.

The α isomer is represented by the following structural formula:

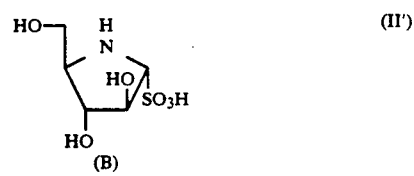

while the β isomer is represented by the following structural formula:

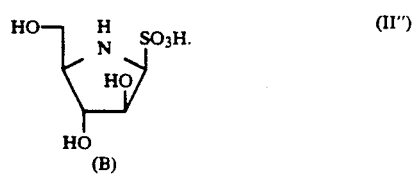

The pyrroline compound (I) and pharmaceutically acceptable salts thereof can be produced by known methods, for example, by culturing *Nectria lucida Hoh-*

*nel* F-4490 (ATCC 20722), as described in Japanese Kokai Tokkyo Koho No. 62-36355.

The pyrroline-sulfurous acid adduct (II) or a pharmaceutically acceptable salt thereof can be produced by reacting the compound (I) or a salt thereof with a reagent capable of converting a group of the formula:

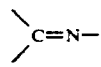

to a group of the formula:

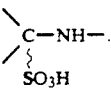

As preferred examples of such reagent, there may be mentioned sulfur dioxide in the presence of water, sulfurous acid, and an alkali metal bisulfite such as sodium bisulfite or potassium bisulfite.

This reaction is carried out in a conventional manner. The most preferable solvent is water. While the reaction temperature is not critical, the reaction is generally carried out under cooling to heating.

The pyrroline-sulfurous acid adduct (II) derived from the pyrroline compound (I) and pharmaceutically acceptable salts of such adduct are more readily crystallizable as compared with the pyrroline compound (I), and that they are very stable and less hygroscopic than the pyrroline compound (I), hence they are more suited for use as drugs.

The pyrroline compound (I), the sulfurous acid adduct (II) derived therefrom and pharmaceutically acceptable salts of these are useful in the prophylaxis and/or treatment of various retrovirus infections, in particular AIDS and ARC, in man and animals.

Furthermore, the pyrroline-sulfurous acid adduct (II) and pharmaceutically acceptable salts thereof have antiinflammatory activity and are useful as antiinflammatory agents as well.

The following test examples are illustrative of the effects of the present invention.

TEST 1

Inhibitory effect on the cytopathic effect of HIV

The inhibitory effect of the compound (I) on the cytopathic effect (syncytium formation) by HIV infection on T lymphocytes was evaluated in the following manner.

(1) CEM cells infected with LAV-1 were washed twice with RPMI 1640 medium and a cell suspension (1 × 10$^6$ cells/ml) was prepared using the same medium. The suspension was distributed in 100-μl portions into culture tubes (16 × 125 mm). Complete medium*[1] containing the compound (I) in several specified concentrations was added to the culture tubes and incubation was performed in the presence of 5% carbon dioxide a 37° C. for 3 days.

The LAV-1-infected CEM cells thus cultured were washed twice with RPMI 1640 medium and then adjusted to 4 × 10$^5$ cells/ml with the complete medium.

[*1: RPMI 1640 medium supplemented with 20% fetal calf serum, 2.5 mM glutamine, kanamycin (100 μg/ml) and penicillin G (100 units/ml)]

(2) Molt4 (clone 8) cells were washed twice with RPMI 1640 medium and then adjusted to 2 × 10$^6$ cells/ml with the complete medium.

(3) The LAV-1-infected CEM cell suspension in complete medium prepared in (1) and the Molt4 (clone 8) cell suspension in complete medium prepared in (2) were respectively distributed in 50-μl portions into 96 well flat bottomed tissue culture plate, followed by further addition of 50 μl of each solution of the compound (I) in complete medium to each well, which was, in advance, prepared to give a final concentration of compound (I) of 100 μg/ml, 50 μg/ml, 20 μg/ml or 10 μg/ml (the final volume in each well being 150 μl).

(4) The above tissue culture plate was incubated at 37° C. in the presence of 5% carbon dioxide for 16 hours and then the giant cells resulting from cytopathic alteration of Molt4 (clone 8) cells were counted within the visual field of a microscope (magnification × 400). The results thus obtained are shown below in Table 1.

The compound (II) was also evaluated for the same inhibitory effect (the α isomer, i.e. the compound (II'), was selected as a representative of the compound (II)). The results obtained are shown below in Table 2.

TABLE 1

| Inhibitory effect of the compound (I) on the cytopathic effect of HIV ||
|---|---|
| Concentration of the compound (I) (μg/ml) | Number of giant cells* |
| 0 | 260.5 |
| 10 | 246.5 |
| 20 | 147.5 |
| 50 | 44.5 |
| 100 | 9.5 |

*Mean of two countings.

TABLE 2

| Inhibitory effect of the compound (II') on the cytopathic effect of HIV ||
|---|---|
| Concentration of the compound (II') (μg/ml) | Number of giant cells* |
| 0 | 173.0 ± 2.0 |
| 1 | 119.5 ± 16.5 |
| 3 | 106.0 ± 19 |
| 10 | 89.0 ± 10 |
| 30 | 53.5 ± 8.5 |
| 100 | 26.5 ± 3.5 |

*Mean ± SD.

TEST 2

Inhibitory effect on the induction of splenomegaly by Friend leukemia virus

Male C3H/HeN mice (5 weeks old) were intraperitoneally inoculated with 3.1 × 10$^1$ MID$_{50}$/mouse of Friend leukemia virus (in 0.2 ml) and then, after this infection procedure, the active ingredient [compound (I) or compound (II)] of the present invention was administered at a specified dose in the form of a solution in sterile physiological saline by the route specified below (Experiment 1 or 2). On day 14 after infection, the mice were sacrificed by exsanguination and the spleen weight (in mg) was measured for evaluating the inhibitory effect of the compound (I) and (II) on the induction of splenomegaly. In each experiment, the control group consisted of mice given no active ingredient after infection with Friend leukemia virus. The percent inhibition of infection was calculated as follows:

Percent inhibition (%) =

$$\left[ 1 - \frac{\frac{\text{Spleen weight (mg) after} - \text{Spleen weight (mg)}}{\text{drug administration}} - \frac{\text{in normal mice}}{\text{Spleen weight (mg) in} - \text{Spleen weight (mg)}}}{\text{control group} \quad \text{in normal mice}} \right] \times 100$$

(1) Experiment 1: Intravenous administration of the compound (I)

The compound (I) was intravenously administered 4 hours after infection (day 0) and then twice daily on days 1 to 4 and days 7 to 11 (19 times in total). The results thus obtained are shown in Table 3.

TABLE 3

Inhibitory effect of compound (I) (intravenously administered) on the induction of splenomegaly by Friend leukemia virus

| Active ingredient | Dose (mg/kg/ administration) | Spleen weight* (mg) | Inhibition (%) |
|---|---|---|---|
| Compound (I) | 20 | 840 ± 421 | 29 |
| | 80 | 667 ± 241 | 46 |
| Control | — | 1149 ± 220 | — |

*Mean of 10 mice; mean normal mouse spleen weight: 92 ± 3 mg.

(2) Experiment 2: Oral administration of the compound (II)

The compound (II) was orally administered 1 hour after infection and then according to the same schedule as in Experiment 1. The results obtained are shown in Table 4.

The compound (II) used was in the α form, namely the compound (II').

TABLE 4

Inhibitory effect of the compound (II') (orally administered) on the induction of splenomegaly by Friend leukemia virus

| Active ingredient | Dose (mg/kg/ administration) | Spleen weight* (mg) | Inhibition (%) |
|---|---|---|---|
| Compound (II') | 10 | 875 ± 71 | 20 |
| Control | — | 1073 ± 26 | — |

*Mean of 8 mice; mean normal mouse spleen weight: 79 ± 2 mg.

Friend leukemia virus used in the above test is known to be a lymphotropic retrovirous, like HIV. Since the extent of splenomegaly in mice induced by said virus is proportional to the proliferation of said virus, the inhibitory effect of an agent on the proliferation of Friend leukemia virus can be estimated by assaying its inhibitory effect on the splenomegaly in mice. The above test results confirmed that the pyrroline compound (I) and the pyrroline-sulfurous acid adduct (II) can inhibit such splenomegally in mice. Furthermore, the present inventors confirmed that the compounds (I) and (II) can potentiate azidothymidine (AZT) in inhibiting such splenomegaly in mice.

TEST 3

Effect of the compound (II) on Type II collagen-induced arthritis in rats (1) TEST COMPOUND (2R, 3S, 4R, 5R)-3,4-dihydroxy-5-hydroxymethyl-2-pyrrolidinesufonic acid (compound (II'))

(2) TEST METHOD

Animals

Inbred 7-week-old female Lewis rats were handled under specific pathogen-free conditions and acclimated to the new environment for a week before use.

Immunization procedure

Type II bovine collagen was dissolved at 4° C. in 0.01M acetic acid at a concentration of 2 mg/ml. The solution was emulsified in an equal volume of incomplete Freund's adjuvant. Rats were anesthetized with sodium pentobarbital (30 mg/kg, i.p.) and the backs of rats were shaved. Under anesthesia, each rat was immunized with 0.8 ml of the cold emulsion by several intradermal injections on the depilated back and one or two injections into the base of the tail.

Treatment with the test compound

The test compound was dissolved in distilled water and administered orally at various doses in 5 ml/kg. From the day of immunization, the test compound or vehicle was administered once a day for 2 weeks.

Assessment of athritis

The extent of arthritis was expressed as the increase in paw volume of each rat. The volume of both hind legs below the knee joint was measured with a plethysmometer. The rats were immunized on day 0 and the paw volume was measured on day 12 and 14. Mean increases in the paw volume of each group was calculated and the result was expressed as means ± SEM. Each group consisted of 10 rats.

(3) Test result

TABLE 5

Effect of the compound (II') on Type II collagen-induced arthritis in rats

| Dose of the test compound (mg/kg) | Pow volume change (ml, means ± SEM) | |
|---|---|---|
| | 12 day | 14 day |
| normal | 0.03 ± 0.07 | 0.05 ± 0.03 |
| 0 (control) | 0.29 ± 0.13 | 0.41 ± 0.24 |
| 10 | 0.16 ± 0.15 | 0.27 ± 0.21 |
| 32 | 0.13 ± 0.10 | 0.19 ± 0.22 |
| 100 | 0.08 ± 0.11 | 0.06 ± 0.04 |

TEST 4

Acute toxicity testing

The compound (I) was administered to mice (ddY strain, female, 5 weeks old) at a dose of 1 g per kg body weight by intravenous injection. The mice survived, with body weight gains.

The test results mentioned above demonstrate that the compounds of the present invention have good prophylactic and therapeutic effects on infectious disease caused by retrovirus (particularly AIDS), and on inflammation.

For therapeutic administration, the pharmaceutical composition of the present invention can be applied in the form of solid, semisolid or liquid preparations containing the compound (I) or (II), as an active ingredient, in admixture with an organic or inorganic carrier, or excipient suitable for oral or non-oral administration. Thus, the active ingredient may be used in the form of, for example, tablets, pellets, capsules, suppositories, granules, solutions, emulsions, suspensions and other suitable dosage forms in admixture with a generally nontoxic and pharmaceutically acceptable carrier. The carrier which can be used is water, glucose, lactose, gum arabic, gelatin, mannitol, starch paste, magnesium trisilicate, talc, methylcellulose, polyethylene glycol, corn starch, keratin, colloidal silica, potato starch, urea and other carriers suited for use in producing solid, semisolid or liquid dosage forms. Furthermore, auxiliaries, stabilizers, humectants, emulsifiers, buffers, thickeners, colorants, perfumes and other additives that are in conventional use may also be used. The composition may further contain one or more preservatives and/or antimicrobial agents so that the active ingredient in each desired dosage form can stably retain its activity. The content of the active ingredient in the composition should be sufficient for prophylactic purposes or for the desired therapeutic effects to be produced on the process and condition of the disease to be treated.

The composition is administered to humans or animals preferably by intravenous injection, subcutaneous injection or intramuscular injection, or by the oral route, for instance. The dose of the active ingredient contained in the composition according to the invention, namely the pyrroline compound (I) or its sulfurous acid adduct (II) or a pharmaceutically acceptable salt thereof may vary depending on such factors as the age and condition of each individual patient to be treated and the stage or degree of disease. The dose may be selected, for instance, at the level of about 0.1, 1, 10, 50, 100, 250, 500, 1,000 or 5,000 mg per administration and, for prophylactic or therapeutic purposes, the composition is administered generally in a daily dose of about 0.01 to 100 mg (as active ingredient) per kilogram of body weight.

The composition according to the invention may contain, in addition to the active ingredient mentioned above, one or more of other antiinflammatory agents and/or agents for retrovirus infections, which are known in the art.

The following examples are further illustrative of the present invention.

EXAMPLE 1

Production of compound (II')

Sulfur dioxide gas was bubbling into an aqueous solution (0.1 ml) of (3R, 4R, 5R)-3,4-dihydroxy-5-hydroxymethyl-1-pyrroline (100 mg) at 0° C. for 30 minutes. The reaction mixture was then allowed to stand at room temperature for 2 days. Methanol (1.0 ml) was added to the reaction mixture with stirring and the resultant crystals (113 mg) was collected by filtration. The X ray analysis data and the following physicochemical data confirmed that the thus-obtained compound was (2R, 3S, 4R, 5R)-3,4-dihydroxy-5-hydroxymethyl-2-pyrrolidinesulfonic acid [compound (II')].

Melting point: 150°-155° C. (decomposition).
IR (Nujol): 3300, 1560, 1380, 1230, 1210 cm$^{-1}$.
NMR (D$_2$O, δ): 3.69 (1H, ddd, J = 4 Hz, 5 Hz, 10 Hz), 3.96 (1H, dd, J = 5 Hz, 12 Hz), 4.13 (1H, dd, J = 7 Hz, 10 Hz), 4.38 (1H, d, J = 7 Hz), 4.46 (1H, t, J = 7 Hz)
$[\alpha]_D^{22} = +44.4°$ (c = 1.00, water)

EXAMPLE 2

| Compound (I) | 100 mg |
|---|---|
| Lactose | 900 mg |

A preparation for oral administration comprising the above compounds is produced by a conventional manner.

EXAMPLE 3

| Compound (I) | 10 mg |
|---|---|
| Physiological saline | 1 ml |

A preparation for oral administration comprising the above compounds is produced by a conventional manner.

EXAMPLE 4

| Compound (II') | 100 mg |
|---|---|
| Lactose | 900 mg |

A preparation for oral administration comprising the above compounds is produced by a conventional manner.

What we claim is:

1. A method for treating infectious diseases caused by retrovirus which comprises administering a pharmacologically effective amount of a pyrroline compound of the formula:

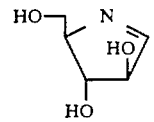

or derivatives thereof of the formula:

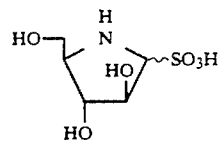

or a pharmaceutically acceptable salt thereof to humans or animals in need of treatment.

2. The method of claim 1 in which the retrovirus is a lymphotrophic retrovirus.

3. A pyrroline-sulfurous acid adduct of the formula:

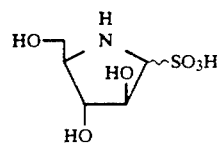

a pharmaceutically acceptable salts thereof.

4. The compound of claim 3, wherein said pyrroline-sulfurous acid adduct is (2R, 3S, 4R, 5R)-3,4-dihydroxy-5-hydroxymethyl-2-pyrrolidinesulfonic acid.

5. A process of preparing a compound of the formula:

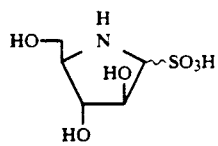

or a salt thereof, which comprises reacting a pyrroline compound of the formula:

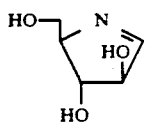

or a salt thereof with at least one sulfonation reagent selected from the group consisting of sulfur dioxide sulfurous acid and alkali metal bisulfites.

6. A pharmaceutical composition which comprises, as an active ingredient, a compound of claim 3, and a pharmaceutically acceptable carrier or excipient.

7. A method for treating inflammation which comprises administering a compound of claim 3 to human or animals.

8. A method for treatment of lymphadenopathy which comprises administering a pharmacologically effective amount of a pyrroline compound of the formula:

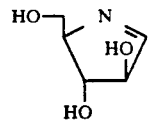

or a derivative thereof of the formula:

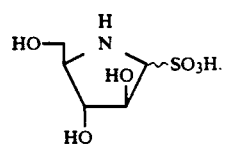

or a pharmaceutically acceptable salt thereof to an individual in need of treatment.

9. A method of claim 1, wherein said composition is administered by intravenous injection, subcutaneous injection, or intramuscular injection.

10. A method of claim 1, wherein said composition is administered orally.

11. The method of claim 8, wherein said composition is administered by intravenous injection, subcutaneous injection, or intramuscular injection.

12. The method of claim 8, wherein said composition is administered orally.

* * * * *